United States Patent [19]

Celmer et al.

[11] 4,287,182

[45] Sep. 1, 1981

[54] **ANTIBIOTICS PRODUCED BY A NEW MICROBE, *CATENULOPLANES JAPONICUS***

[75] Inventors: Walter D. Celmer, New London; Walter P. Cullen, East Lyme; Liang H. Huang, East Lyme; John R. Oscarson, Pawcatuck, all of Conn.; Riichiro Shibakawa, Handa; Junsuke Tone, Chita, both of Japan

[73] Assignee: Pfizer Inc., New York, N.Y.

[21] Appl. No.: 165,407

[22] Filed: Jul. 2, 1980

[51] Int. Cl.³ ............................................. A61K 35/00
[52] U.S. Cl. ..................................... 424/118; 435/169
[58] Field of Search ......................... 424/118; 435/169

[56] References Cited

U.S. PATENT DOCUMENTS 4,029,769  6/1977  Debono ................................ 424/118

*Primary Examiner*—Jerome D. Goldberg
*Attorney, Agent, or Firm*—Connolly and Hutz

[57] ABSTRACT

Antibiotics CP-54,715 and CP-54,716, identified by their analytical characteristics, are produced by fermentation of a new microbial species *Catenuloplanes jaonicus* in a new genus Catenuloplanes and are active against gram-positive and anaerobic infections.

9 Claims, 2 Drawing Figures

Infrared Absorption Spectrum Of CP-54,715

Infrared Absorption Spectrum Of CP-54,716

ANTIBIOTICS PRODUCED BY A NEW MICROBE, *CATENULOPLANES JAPONICUS*

BACKGROUND

This invention relates to two new antibiotics, designated CP-54,715 and CP-54,716, which are produced by a new microbial species *Catenuloplanes japonicus* Huang sp. nov., strains N381-16 (ATCC 31,637) and N406-14 (ATCC 31,638). The antibiotics are active against gram-positive bacteria.

The genus Catenuloplanes appears to be related to the genera of the Actinoplanacae sensu Couch which produce such antibiotics as taitomycin, lipiarmycin, gardimycin and the like. It resembles genera such as Actinoplanes, Amorphosporangium and Dactylosporangium in having motile spores but contains lysine instead of meso-diaminopimelic acid in the cell wall and produces spores arranged in chains instead of enclosed in a sporangial wall.

The genera other than those of the Actinoplanaceae with motile spores have morphological features e.g. morphology and cell wall composition that differ from those of Catenuloplanes. Oerskovia shows some resemblance to the new genus in the lack of meso-DAP in the cell wall, but differs in the absence of aerial mycelium and the mode of spore formation. Kineosporia and Sporichthya are characterized by a cell wall of Type I; the former exhibits the absence of aerial mycelium and the latter the absence of substrate mycelium. Dermatophilus and Geodermatophilus have a different mode of spore formation, a different cell wall type, and do not produce aerial mycelium. Abundant aerial mycelium is produced by Streptoalloteichus and Actinosynnema, which have cell wall types different from that of Catenuloplanes. Streptoalloteichus produces subspherical to peanut shell-shaped sporangia as well as chains of spores; Actinosynnema, as the name implies, forms a synnema on which chains of spores are produced.

SUMMARY

The purified forms of the two antibiotics CP-54,715 and CP-54,716 are produced by fermentation of strains of *Catenuloplanes japonicus* Huang sp. nov. (ATCC 31,637 and ATCC 31,638) and isolation of the more and less polar components respectively of the whole broth at neutral pH.

Antibiotic CP-54,715 is characterized by its solubility in methanol and chloroform; its insolubility in heptane; its elemental analysis of C-49.62%, H-6.16%, N-1.04%, Cl-5.16%; its decomposition point of 166°–176° C.; its $[\alpha]_D^{20}$ rotation of $-8°$ in methanol; its UV max at 289 nm with an extinction coefficient of 29 at 1% concentration in methanol; and its IR spectrum as a suspension in a KBr pellet as shown in FIG. 1.

Antibiotic CP-54,716 is characterized by its solubility in methanol and chloroform; its insolubility in heptane; its elemental analysis of C-50.89%, H-6.60%, N-1.25%, Cl-6.34% its decomposition point of 140°–155° C.; its $[\alpha]_D^{20}$ rotation of $-19°$ C. in methanol; its UV max at 289 nm with an extinction coefficient of 30 at 1% concentration in methanol and its IR spectrum as a suspension in a KBr pellet as shown in FIG. 2.

Fermentation of the microorganisms is accomplished by growth in an aqueous, nutrient fermentation medium containing assimilable sources of carbon, nitrogen and inorganic salts until antibiotic activity is produced.

Either antibiotic may be intravenously or subcutaneously administered alone or as a pharmaceutical composition to treat a gram-positive and anaerobic bacterial infection in a host. The pharmaceutical composition consists of an effective amount of either antibiotic and a pharmaceutical carrier.

DETAILED DESCRIPTION

Figure 1:
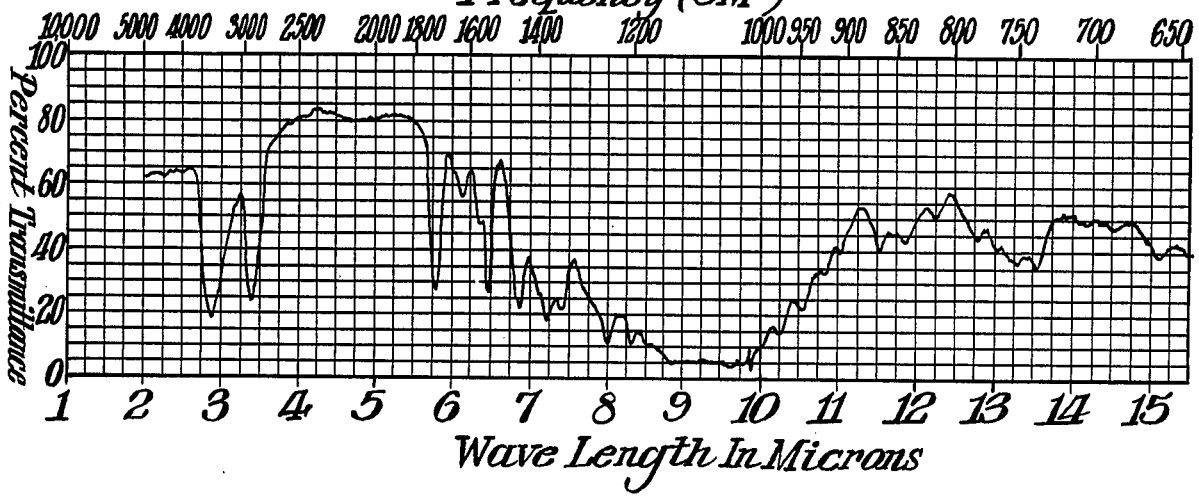

The microorganisms useful for the preparation of the antibiotics were isolated from soil samples from Japan and India and designated as cultures N381-16 and N406-14, respectively. Culture N381-16 is gram-positive, non-acid-fast and is characterized by non-fragmentary, yellowish orange to orange substrate mycelium, sparse aerial mycelium, and spores which are produced in chains and are motile. In addition to glutamic acid, alanine, glucosamine and muramic acid typical of other actinomycete cell wall compositions, the pure cell wall contains lysine, glycine and traces of serine. The whole-cell analyses shows the presence of xylose and traces of arabinose and the absence of LL- or meso-diaminopimelic acid. The culture is described as the new species *Catenuloplanes japonicus* Huang. sp. nov. in the new genus Catenuloplanes Huang gen. nov. N381-16 is designated as the type strain of the new species and has been deposited at the American Type Culture Collection with the accession number 31,637.

Culture N406-14 has the same morphological features and almost all of the biochemical properties as strain N381-16. It differs, however, from the latter in darker colors of colonies ranging from orange, brown to black, the production of dark soluble pigment on some media, the ability to grow at 37° C. but not at 21° C., and the inability to produce acid from melezitose. Until more isolates belonging to the newly proposed genus Catenuloplanes can be isolated and the significance of the cultural differences assessed, the present designation of culture N406-14 as a strain of *Catenuloplanes japonicus* is tentative. N406-14 has been deposited at the American Type Culture Collection with the accession number 31,638.

The following methods can be used to observe the cultural, physiological and morphological features of microorganisms N381-16 and N406-14. An inoculum is prepared by planting the appropriate culture from a freeze-dried lyophil into ATCC #172 broth and growing for 6 days at 28° C. on a shaker. It is then centrifuged for 20 min., washed three times with sterile distilled water and planted on media commonly used for identification of members of the Actinomycetales.

Incubation is made at 28° C. and a reading of results may be made at varying times but most commonly is taken at 14 days. Tables I through VI below list the features of N381-16 and N406-14 determined in this manner. The colors are described in common terminology, but exact colors are determined by comparison with color chips from the Color Harmony Manual, fourth edition. The methods of whole-cell analysis, sugar analysis, cellulose utilization, organic acid utilization, carbohydrate utilization and the formulas for the identification media are well known to those familiar with the art.

TABLE I

Cultural Description of N381-16 on Various Media

Yeast Extract-Malt Extract Agar—Growth good, yellowish orange (4 ea to 4 ga), slightly raised and finely wrinkled, with a few raised small dots, no aerial mycelium; reverse same as surface; soluble pigment pale yellowish.

Oatmeal Agar—Growth moderate, pale orange to yellowish orange (3 ca, 4 ea to 4 ga) thin, smooth, sparse aerial mycelium observed only under microscope; reverse same as surface; no soluble pigment.

Inorganic Salts-Starch Agar—Growth good, pale orange to orange (4 ea to 4 na), thin and smooth at the center, moderately raised and wrinkled toward ends of streaks, no aerial mycelium; reverse same as surface; soluble pigment pale yellowish (between 2 ca and 2 ea).

Glycerol-Asparagine Agar—Growth moderate, pale yellowish orange (3 ea to 3 ga), thin, smooth, with a few small bumps, sparse aerial mycelium observed only under microscope; reverse same as surface; no soluble pigment.

Gelatin Agar—Growth good, orange yellow (near 3 la to 3 na), slightly raised, smooth but wrinkled near edge, sparse aerial mycelium observed only under microscope; reverse same as surface; no soluble pigment.

Starch Agar—Growth good, orange yellow (3 ia), slightly raised, smooth but wrinkled near edge, no aerial mycelium; reverse same as surface; no soluble pigment.

Potato Carrot Agar—Growth poor to moderate, colorless to dull white, thin, submerged with a spreading edge, sparse aerial mycelium observed only under microscope; reverse same as surface; no soluble pigment.

Tap Water Agar—Growth scant, colorless, thin, submerged, smooth, sparse aerial mycelium observed only under microscope; reverse same as surface; no soluble pigment.

Czapek-Sucrose Agar—Growth good, dull white to pale yellowish orange (3 ea), thin, smooth, slightly shiny, with a moderately spreading edge, no aerial mycelium; reverse same as surface; soluble pigment very pale yellowish.

Glucose-Asparagine Agar—Growth good, yellowish orange (between 3 ga and 4 ga), slightly raised, smooth, with a few small bumps, no aerial mycelium; reverse same as surface; soluble pigment very pale yellowish.

Glucose-Yeast Extract Agar—Growth moderate to good, orange (4 ea to 4 ga), moderately to highly raised, slightly to strongly wrinkled, no aerial mycelium; reverse same as surface; no soluble pigment.

Emerson's Agar—Growth moderate to good, dull white, thin, wrinkled, with a few small bumps, no aerial mycelium; reverse same as surface; no soluble pigment.

Nutrient Agar—Growth moderate, pale orange yellow (3 ea to 3 ga), thin, smooth, no aerial mycelium; reverse same as surface; no soluble pigment.

Bennett's Agar—Growth good, orange (4 ia to 4 la), slightly raised but raised near ends of streaks, wrinkled, no aerial mycelium; reverse same as surface; no soluble pigment.

Gordon and Smith's Tyrosine Agar—Growth moderate, yellowish orange (near 3 ia), thin, smooth, no aerial mycelium; reverse same as surface; soluble pigment pale brown (near 2 ic).

Casein Agar—Growth good, bright orange (4 na o 4 pa), slightly raised, wrinkled, no aerial mycelium; reverse same as surface; no soluble pigment.

Calcium Malate Agar—Growth moderate, pale orange yellow (near 3 ea to 3 ga), thin, smooth, no aerial mycelium; reverse same as surface; soluble pigment very pale yellowish.

TABLE II

Cultural Description of N406-14 on Various Media

Yeast Extract-Malt Extract Agar—Growth good, orange (near 5 ia), slightly raised, wrinkled, no aerial mycelium; reverse same as surface; soluble pigment yellowish.

Oatmeal Agar—Growth moderate, light brownish orange (4 ea to 3 ic), thin, smooth to slightly roughened, aerial mycelium observed only under microscope; reverse same as surface; soluble pigment pale yellowish.

Inorganic Salts-Starch Agar—Growth moderate to good, brownish (4 ne) with a brownish orange (4 to 4 pc) edge, smooth but wrinkled near the edge, no aerial mycelium; reverse brownish to brownish orange; soluble pigment yellowish orange (3 ea).

Glycerol-Asparagine Agar—Growth poor to moderate, colorless, cream, to pale pinkish (3 ca), thin, smooth, sparse aerial mycelium observed only under microscope; reverse same as surface; no soluble pigment.

Gelatin Agar—Growth good, purplish to violet (6 ie to 6 ni), slightly raised, smooth to slightly roughened, with short greyish aerial mycelium; reverse same as surface; soluble pigment purplish brown (3 le to 5 ie).

Starch Agar—Growth good, brown to black (5 ng), slightly raised, roughened to wrinkled, no aerial mycelium; reverse same as surface; soluble pigment brown (3 ne).

Potato Carrot Agar—Growth moderate, pale brownish (3 gc to 3 ie), thin, smooth to slightly bumpy, with sparse aerial mycelium; reverse same as surface; no soluble pigment.

Tap Water Agar—Same as N381-16 except aerial mycelium is lacking.

Czapek-Sucrose Agar—Growth good, orange (near 4 ge), thin, smooth, with scattered small white patches of aerial mycelium; reverse same as surface; soluble pigment pale yellowish.

Glucose-Asparagine Agar—Growth moderate, orange to bright orange (4 la to 4 pa), thin to slightly raised, smooth to slightly roughened, no aerial mycelium; reverse same as surface; no soluble pigment.

Glucose-Yeast Extract Agar—Growth good, black but orange, pale yellowish orange (4 ga) near ends of streaks, moderately raised, roughened to wrinkled, with small black exudate, no aerial mycelium; reverse same as surface; soluble pigment black.

Emerson's Agar—Growth moderate, pale orange (4 ea), moderately raised, roughened; no aerial mycelium; reverse same as surface; no soluble pigment.

Nutrient Agar—Growth moderate, bright orange (4 na to 4 pa), thin, smooth to slightly roughened, no aerial mycelium; reverse same as surface; no soluble pigment.

Bennett's Agar—Growth moderate, orange (4 ia), thin to slightly raised, smooth to slightly roughened, no aerial mycelium; reverse same as surface; no soluble pigment.

Gordon and Smith's Tyrosine Agar—Growth moderate, black, thin, or occurring as isolated dots, with sparse greyish aerial mycelium; reverse same as surface; soluble pigment black.

Casein Agar—Same as N381-16 except colonies are coarsely wrinkled.

Calcium Malate Agar—Growth moderate, pale yellowish orange (between 3 ea and 4 ea), thin, smooth, with short aerial mycelium; reverse same as surface; no soluble pigment.

TABLE III

Morphological Properties of N381-16 and N406-14

Fragmentation of substrate mycelium and the development of aerial mycelium on Czapek-sucrose agar—observation once every week up to three weeks: no fragmentation of the substrate mycelium; after one week of incubation monopodial or dichotomous branched aerial mycelium developed; origins of the branches could not be traced at a later stage of development; spore chains and aerial mycelium often aggregate into clusters resembling a flower or a sporodochium—compact and flat at the center but filamentous toward the edge.

Morphological observations on the 14-day-old culture grown on oatmeal agar: aerial mycelium lacking or short; spore chains arranged in spirals of 1-2 turns, hooked or rarely flexuous, arising from the substrate mycelium or the aerial mycelium, single or often aggregated in clusters, several spores per spore chain; spores rod-shaped, straight or curved, $2-4\times0.9-1.0$ μm, smooth as revealed by scanning electron microscopy, motile when suspended in sterile distilled water, with peritrichous flagella as revealed by transmission electron microscopy.

TABLE IV

Biochemical Properties of N381-16 and N406-14

I. Gram-positive; non-acid-fast; no melanin produced; hydrogen sulfide produced; no reduction of nitrate to nitrite on both organic and dextrose nitrate broths; gelatin liquefaction positive; hydrolysis of starch positive; hydrolysis of hippurate negative; decomposition of adenine, xanthine and hypoxanthine negative; decomposition of cellulose negative; decomposition of calcium malate, tyrosine, esculin and urea positive; no resistance to lysozyme; coagulation and clearing on milk.

II. Utilization of organic acids: acetate, lactate, malate, pyruvate and succinate utilized; benzoate, citrate, mucate, oxalate, propionate, dextrin and phenol not utilized.

III. Acid production from carbohydrates: acid produced from arabinose, cellobiose, fructose, galactose, glucose, glycerol, inositol, lactose, maltose, mannitol, mannose, melibiose, melezitose, α-methyl-d-glucoside, raffinose, rhamnose, ribose, salicin, starch, sucrose, trehalose and xylose; acid not produced from adonitol, dulcitol, erythritol, sorbitol and sorbose.

IV. Carbohydrate utilization: arabinose, cellobiose, fructose, galactose, glucose, glycerol, inositol, lactose, maltose, mannitol, mannose, melezitose, melibiose, α-methyl-d-glucoside, raffinose, rhamnose, ribose, salicin, starch, sucrose, trehalose and xylose utilized; adonitol, dulcitol, erythritol, sorbitol and sorbose not utilized.

TABLE V

Temperature Relation of N381-16 and N406-14 Growth

N381-16 shows good growth at 21° and 28° C.; N406-14 shows good growth at 28° and 37°; both show no growth at 5°, 45° and 50° C.

TABLE VI

Whole Cell and Cell Wall Analyses of N381-16

Major amounts of lysine, glutamic acid, glycine, alanine, glucosamine, muramic acid and some serine present but no diaminopimelic acid; whole-cell sugar pattern of the Type D showing major amounts of xylose and traces of arabinose; whole-cell amino acid analysis—no LL- or meso-diaminopimelic acid in the hydrolysate.

Cultivation of *Catenuloplanes japonicus* ATCC 31,367 or ATCC 31,638 is usually accomplished in aqueous nutrient media at a temperature of 24°–36° C., and under submerged aerobic conditions with agitation. Nutrient media which are useful for such purposes include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic may be obtained from a growth of the culture on a slant or Roux bottle. A suitable solid medium is ATCC medium No. 172. The growth may be used to inoculate either shake flasks or inoculum tanks, or alternatively, the inoculum tanks may be seeded from the shake flasks. Growth in shaken flasks will generally have reached its maximum in 2 to 4 days whereas growth in submerged inoculum tanks will usually be at the most favorable period in 2 to 3 days. Substantial antibiotic activity is obtained in the final fermentor stage in approximately 3 to 5 days.

The process of antibiotic production is conveniently followed during fermentation by biological assay of the broth employing a sensitive strain of *Staphylococcus aureus* or *Bacillus subtilis*. Standard plate assay technique is employed in which the zone of inhibition surrounding a filter paper disc saturated with the broth is used as a measure of antibiotic potency.

The antibiotics may be isolated and recovered from whole fermentation broth by extracting at neutral pH with an organic solvent such as chloroform, ethyl acetate or methyl isobutyl ketone. They may be separated by column or high pressure liquid chromatography. Thin layer chromatography employing silica gel is a useful tool for antibiotic analysis of the fermentation media and the isolated and separated materials.

Antibiotics CP-54,715 and CP-54,716 exhibit inhibitory action against the growth of a number of gram-positive and anaerobic microorganisms as shown in Table VII. The test organism is inoculated in a series of test tubes which contain nutrient medium and various concentrations of the test antibiotic. Activity is determined as the minimal concentration of antibiotic in mcg/ml which inhibits the growth of the organism over a period of 24 hours.

TABLE VII

| Organism | | Activity of Antibiotic CP-54,715 (mcg/ml) | Activity of Antibiotic CP-54,716 (mcg/ml) |
|---|---|---|---|
| Staphylococcus aureus | 01A005 | 0.3 (avg. 3 tests) | 0.10 |
|  | 01A052 | 0.2 | 0.20 |
|  | 01A110 | 0.2 | 0.78 |
|  | 01A400 | 0.39 | 0.78 |
| Staphylococcus epidermidis | 01B111R | 0.39 | 0.78 |
|  | 01B087RR | 0.39 | 0.20 |
| Streptococcus faecalis | 02A006 | 0.20 | 0.10 |
| Streptococcus pyogenes | 02C203 | 0.0125 | 0.0125 |
| Neisseria sicca | 66C000 | 1.56 | 1.56 |
| Bacillus subtilis | 06A001 | 1.56 | 0.39 |
| Pasteurella multocida | 59A001 | 3.12 | 3.12 |
| Moraxella bovis | 93A001 | 0.39 | NT |
| Bacteroides vulgatis | 78EC032 | 0.78 | NT |
| Haemophilis parahaemolyticus | 54B002G | 25 | NT |
| Treponema hyodysenteriae | B100 | 25 | NT |
|  | B141 | 25 | NT |

The antibiotics did not show activity at concentrations up to 50 mcg/ml against gram-negative bacteria such as E. coli, Ps. aeruginosa, Klebs. pneumoniae, Serr. marcescens and Ent. aerogenes.

The antibiotics also exhibited anti-infectious activity in vivo by preventing staphylococcal infection in mice dosed s.c. with a sterile ethanolic solution of the test antibiotic. Subcutaneous administration produced PD 50's of 8.5 and 13 for CP-54,715 and CP-54,716, respectively. The antibiotics were not active orally in this test.

The antibiotics are effective for treatment of a gram-positive and anaerobic infection in a host and may be administered i.v. or s.c. either alone or with a pharmaceutical carrier. Ultimate choice of route and dose is made by the attending physician and is based upon the patient's unique condition.

Combination with appropriate pharmaceutical carriers is accomplished by methods well known to the pharmacist's art. For purposes of subcutaneous administration, solutions of the antibiotic in sesame or peanut oil or in aqueous propylene glycol may be employed, as well as sterile aqueous or alcoholic solutions. Such aqueous solutions should be suitably buffered if necessary and the liquid diluent may first be rendered isotonic with sufficient saline or glucose. These aqueous and alcoholic solutions are also suitable for intravenous injection.

The following examples describe the invention in greater detail.

EXAMPLE 1

Fermentation of *Catenuloplanes japonicus* N381-16 (ATCC 31,637) and isolation of CP-54,715 and CP-54,716

A sterile aqueous medium having the following composition was prepared:

|  | Grams/liter |
|---|---|
| Glucose | 10.0 |
| Soluble starch | 20.0 |
| Yeast extract | 5.0 |
| NZ Amine A | 5.0 |
| $CoCl_2$ | 0.002 |
| $CaCO_3$ | 4.0 |
| Tap water to 1 L., pH to 7.1–7.2 | |

The medium was distributed 40 ml per 300 ml shake flask then sterilized at 120° C. and 15 p.s.i. for 30 minutes. After cooling the medium was inoculated with a vegetative cell suspension from the slant culture *Catenuloplanes japonicus* (ATCC 31,637) grown on ATCC 172 medium in agar. The flasks were shaken at 28° C. on a rotary shaker having a displacement of 1½ to 2½" at 150 to 200 cycles per minute (CPM) for three to four days, then used to inoculate a four liter fermentation vessel containing two liters of one of the following media:

| JD | grams/liter | CAM-2 | grams/liter |
|---|---|---|---|
| Cerelose | 1.0 |  |  |
| Casein | 5.0 | Starch | 20 |
| Starch | 5.0 | Soybean Flour | 10 |
| Corn Steep Liquor | 5.0 cc | Corn Steep Liquor | 1 cc |
| Calcium Carbonate | 3.0 | Ferrous Sulfate | 0.1 |
| Cobalt Chloride | 0.002 | Cobalt Chloride | 0.002 |
| Water to 1 liter, pH | 6.9–7.0 | Calcium Carbonate | 2 |

One milliliter of L61 was added as antifoaming agent, and the vessels sealed and sterilized at 120° C. and 15 p.s.i. for 45 minutes. The pots were inoculated with one (2%) or two (4%) inoculum flasks, fermented for 2 to 5 days at 30° C., stirred at 1700 revolutions per minute (RPM) and air sparged through the broth at one volume per volume per minute. When fermentation was complete (based on antibiotic disc assay versus *B. subtilis* ATCC 6633) the fermentors were stopped and the whole broth was extracted two times with ⅓ to ½ volume of a solvent such as methylisobutyl ketone or n-butanol at neutral pH. The solvent was separated from the aqueous phase by aspiration, sparkled, and concentrated in vacuo to yield the antibiotics CP-54,715 and CP-54,716 as a viscous oil.

The bioactivity of the broth, and subsequent recovery steams was followed by using a sensitive strain of *Bacillus subtilis* ATCC 6633 or *Staphylococcus aureus* ATCC 6538. The components in the broth and recovery streams were visualized by using fluorescent silica gel plates in the following system: chloroform/methanol 9:1 and visualizing the antibiotics under ultraviolet light at 254 nm. The plate was also overlayed with agar seeded with either *S. aureus* or *B. subtilis* and incubated at 37° C. for 16 hours to detect the antibiotic.

Scale-up in large fermentors was carried out by preparing shake flasks containing 0.7 liters of M172M medium. The shake flask inoculum was fermented for 3 to 4 days at 28° C., composited into two side-arm bottles then used to inoculate two 2000 gallon fermentors each containing 1200 gallons of CAM-2 medium. Approximately 6 liters (0.1%) of inoculum was used in each tank. One fermentor, after running 5 days, was harvested (1200 gallon). The whole broth was extracted with 1/5 volume of methyl isobutyl ketone at natural pH, separated on a Podbielnack extractor and the solvent concentrated in vacuo to a syrup containing a mixture of the antibiotics CP-54,715 and CP-54,716.

EXAMPLE 2

Isolation and Separation of CP-54,715 and CP-54,716

One thousand gallons of the whole broth of fermented *Catenuloplanes japonicus* ATCC 31,637, grown as described in Example 1, was extracted with methyl isobutyl ketone. The methyl isobutyl ketone was evaporated under vacuum to give approximately 1 kilogram of a dark oil containing a mixture of the antibiotics.

This oil was poured slowly into six liters of stirring heptane. After stirring for 10 minutes the mixture was allowed to settle and the heptane was decanted off. The residue was dissolved in chloroform and evaporated under vacuum to a syrup (approximately 200 ml). The syrup was poured into two liters of fresh heptane, while stirring, and the solids which precipitated out were collected by filtration on a sintered glass funnel. The solids were washed with a small amount of ether and air dried to yield 39 grams of a crude mixture of the antibiotics.

The solids were fractionated by column chromatography on silica gel. A 2.54×95 cm glass column was packed with column grade silica gel in chloroform-methanol (97:3). Five grams of the antibiotic mixture was put on the column and was eluted with the same solvent system. The flow rate was 10 ml/min and 10 ml cuts were taken. The column cuts were examined by thin layer chromatography as described previously. This procedure was repeated until all of the antibiotic mixture had been chromatographed.

The cuts containing CP-54,715 from all columns were combined and evaporated under vacuum, then rechromatographed as described above. The cuts containing CP-54,715 were again combined and evaporated under vacuum. The residue was dissolved in chloroform and stirred for 15 minutes with 1 gram of activated carbon. The solution was then filtered and evaporated under vacuum giving 1.5 grams of an off-white solid CP-54,715.

The cuts containing CP-54,716 were processed in the same manner to give 1.4 grams of CP-54,716.

Table VIII below provides the analytical data obtained for CP-54,715 and CP-54,716.

TABLE VIII

Analytical Data

CP-54,715

Elemental Analysis: C-49.62%, H-6.16%, N-1.04%, Cl-5.16%.
UV Spectrum: $\lambda_{max}$ 289 nm (methanol) $E_1\ _{cm}^{1\%}=29$
Optical Rotation: $[\alpha]_D^{20}=-8°$ (c=1, methanol)
Decomposition Point: 166°-176° C.

The distinguishable bands in the infrared spectrum over the region 2 to 14 microns are as follows (KBr disc): 2.90, 3.40, 5.80, 6.10, 6.45, 6.85, 7.20, 8.00, 8.35, 8.90, 9.65, 10.25, 10.55, 11.55, 12.75, 13.00, 13.55. (FIG. 1)

CP-54,716

Elemental Analysis: C-50.89%, H-6.60%, N-1.25, Cl-6.34%.
UV Spectrum: $\lambda_{max}$ 289 nm (methanol) $E_1\ _{cm}^{1\%}=30$
Optical Rotation: $[\alpha]_D^{20}=-19°$ (c=1, methanol)
Decomposition Point: 140°-155° C.

Figure 2:
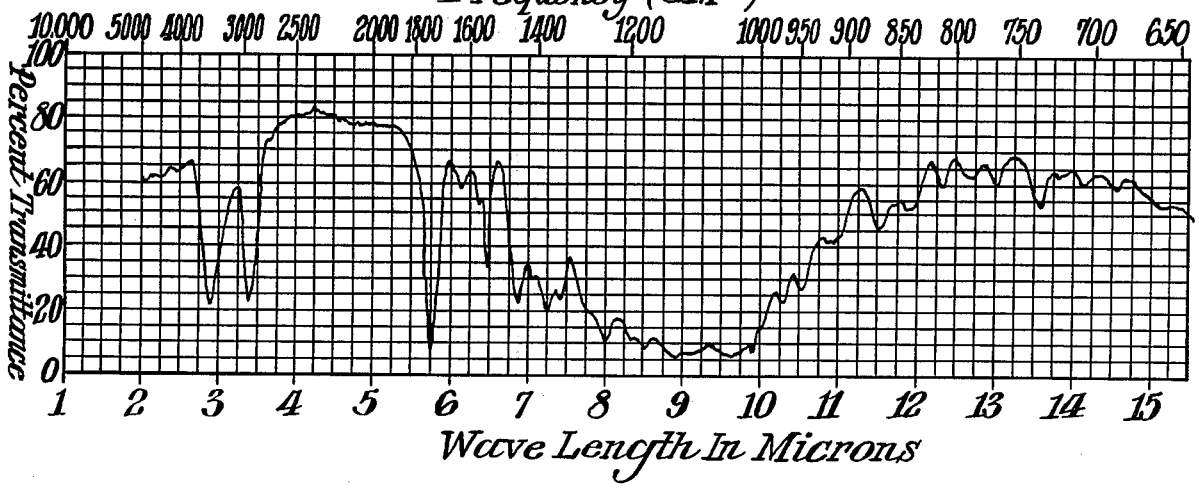

The distinguishable bands in the infrared spectrum over the region 2 to 14 microns are as follows (KBr disc): 2.90, 3.40, 5.80, 6.10, 6.50, 6.90, 7.25, 7.40, 8.00, 8.35, 9.05, 9.65, 10.25, 10.55, 11.05, 13.55. (FIG. 2)

We claim:

1. The antibiotic CP-54,715 which is soluble in methanol and chloroform; insoluble in heptane; has an elemental analysis of C, 49.62%; H, 6.16%; N, 1.04%; and Cl, 5.16%; a decomposition point of 166°-176° C.; an $[\alpha]_D^{20}$ rotation of $-8°$ in methanol; a UV max at 289 nm with an extinction coefficient of 29 at 1% concentration in methanol and an IR spectrum as a suspension in a KBr pellet as shown in FIG. 1.

2. The antibiotic CP-54,716 which is soluble in methanol and chloroform; insoluble in heptane; has an elemental analysis of C, 50.89%; H, 6.60%; N, 1.25%; Cl, 6.34%; a decomposition point of 140°-155° C.; an $[\alpha]_D^{20}$ rotation of $-19°$ in methanol; a UV max at 289 nm with an extinction coefficient of 30 at 1% concentration in methanol and an IR spectrum as a suspension in a KBr pellet as shown in FIG. 2.

3. A process for producing the antibiotic of claim 1 or 2, which comprises:
   growing the microorganism *Catenuloplanes japonicus* ATCC 31,637 or ATCC 31,638 in an aqueous, nutrient, fermentation medium containing assimilable sources of carbon, nitrogen and inorganic salts, until antibiotic activity is produced.

4. A process of claim 3 wherein the antibiotic is separated from the fermentation medium.

5. A process of claim 3 wherein a mixture of the two antibiotics is produced.

6. A process of claim 5 wherein the mixture of antibiotics is separated from the fermentation medium.

7. A process of claim 6 wherein the mixture is chromatographed to separate the two antibiotics.

8. A pharmaceutical composition for inhibiting growth of gram-positive and anaerobic microorganisms, said composition comprising an antibiotic of claim 1 or 2 and a pharmaceutical carrier, the amount of said antibiotic being sufficient to inhibit the growth of the gram-positive and anaerobic microorganisms.

9. A method of treating a host infested with a gram-positive or anaerobic infection which comprises intravenously or subcutaneously administering to said host an antibiotic of claim 1 or 2 in an amount sufficient to combat said infection.

* * * * *